Patent Number: 5,066,843
Date of Patent: Nov. 19, 1991

[54] HEAT RESISTANT AND LIGHT WEIGHT CONTAINER FOR MATERIALS TO BE ASHED, AND PROCESS FOR MANUFACTURE THEREOF

[75] Inventor: Robert N. Revesz, Monroe, N.C.
[73] Assignee: CEM Corporation, Matthews, N.C.
[21] Appl. No.: 298,553
[22] Filed: Jan. 18, 1989
[51] Int. Cl.$^5$ .................... H05B 6/80; G01N 31/12
[52] U.S. Cl. .................... 219/10.55 R; 264/26; 422/78; 436/155
[58] Field of Search ............... 219/10.55 R, 10.55 E, 219/10.55 F, 10.55 M; 126/390; 264/25, 26, 345, 346, DIG. 46; 422/78, 21; 436/155

[56] References Cited

U.S. PATENT DOCUMENTS

| | | | |
|---|---|---|---|
| 3,731,037 | 5/1973 | Levinson | 219/10.55 E |
| 3,773,669 | 11/1973 | Yamauchi et al. | 219/10.55 E |
| 4,003,368 | 1/1977 | Maxel | 219/10.55 E |
| 4,495,775 | 1/1985 | Young et al. | 206/0.7 |
| 4,565,669 | 1/1986 | Collins et al. | 219/10.55 R |

Primary Examiner—Philip H. Leung
Attorney, Agent, or Firm—Raymond F. Kramer

[57] ABSTRACT

A container for an ashable material, to be ashed by heat in an ashing furnace, especially one heated by microwave radiation onto microwave absorptive elements thereof, comprises a heat resistant, walled container which is light weight, microwave transmissive and porous, and which is of quartz microfibers that are held in desired walled container form, preferably in substantially flat cylindrical form. Such a container is made by shaping a heat resistant, light weight, microwave transmissive and porous non-woven sheet of quartz microfibers to container form and heating and curing such sheet in such form, preferably after moistening it with water, whereby a form-retaining container results that can be successfully employed to hold ashable analytic samples during ashings thereof.

15 Claims, 2 Drawing Sheets

HEAT RESISTANT AND LIGHT WEIGHT CONTAINER FOR MATERIALS TO BE ASHED, AND PROCESS FOR MANUFACTURE THEREOF

The present invention relates to a container which is suitable for holding an ashable material to be ashed in a high temperature ashing furnace. More particularly, it relates to such a container which is heat resistant, light in weight, microwave transmissive and porous, and which is made of quartz microfibers which are held together in walled container form.

Prior to the present invention quartz fiber discs had been disclosed as supports for samples to be ashed by heat generated by directing microwave energy onto microwave absorptive materials. In U.S. Pat. No. 4,565,669, issued to Collins and Hargett, a quartz fiber support pad and a cover of the same material were utilized to confine an ashable analytic sample to be analyzed during the ashing of such sample by heat generated by directing microwave radiation at microwave absorptive silicon carbide under such a support pad. U.S. Pat. No. 4,565,669 represents the closest art known to applicant but it does not describe or suggest the subject matter of the present invention and does not make it obvious, and the ashing process of the patent does not result in the improved ashing that is obtainable with the invented container.

In accordance with this invention a container for an ashable material, which material may be ashed by heat generated by microwave radiation of microwave absorptive elements in an ashing furnace, comprises a heat resistant, walled container which is light in weight, microwave transmissive and porous, and is made of quartz microfibers which are held in walled container form. Also within the invention is a process for manufacturing such a container by shaping of a light weight, microwave transmissive and porous sheet of quartz microfibers to container form and heating such sheet in such form, preferably after wetting and drying it, whereby a form retaining container results, which is resistant to ashing temperatures and other ashing conditions.

The invented containers are especially useful in conjunction with microwave ashing apparatuses like that described in an application for patent, Ser. No. 07/298,554, of Michael J. Collins, and Wyatt P. Hargett, entitled Microwave Ashing and Analytical Apparatuses, Components and Processes, which is being filed in the U.S. Patent and Trademark Office on the same day as the present application. The disclosure of such application is incorporated herein by reference, together with the disclosure of U.S. Pat. No. 4,565,669. However, the invented containers also find use in other ashing applications, such as those conducted in conventional muffle furnaces, and in other heating operations, including fusions and dry ashings (wherein ash is produced for subsequent analyses, such as for heavy metals).

The invention will be readily understood by reference to this specification, including the accompanying drawing, in which.

Figure 1:
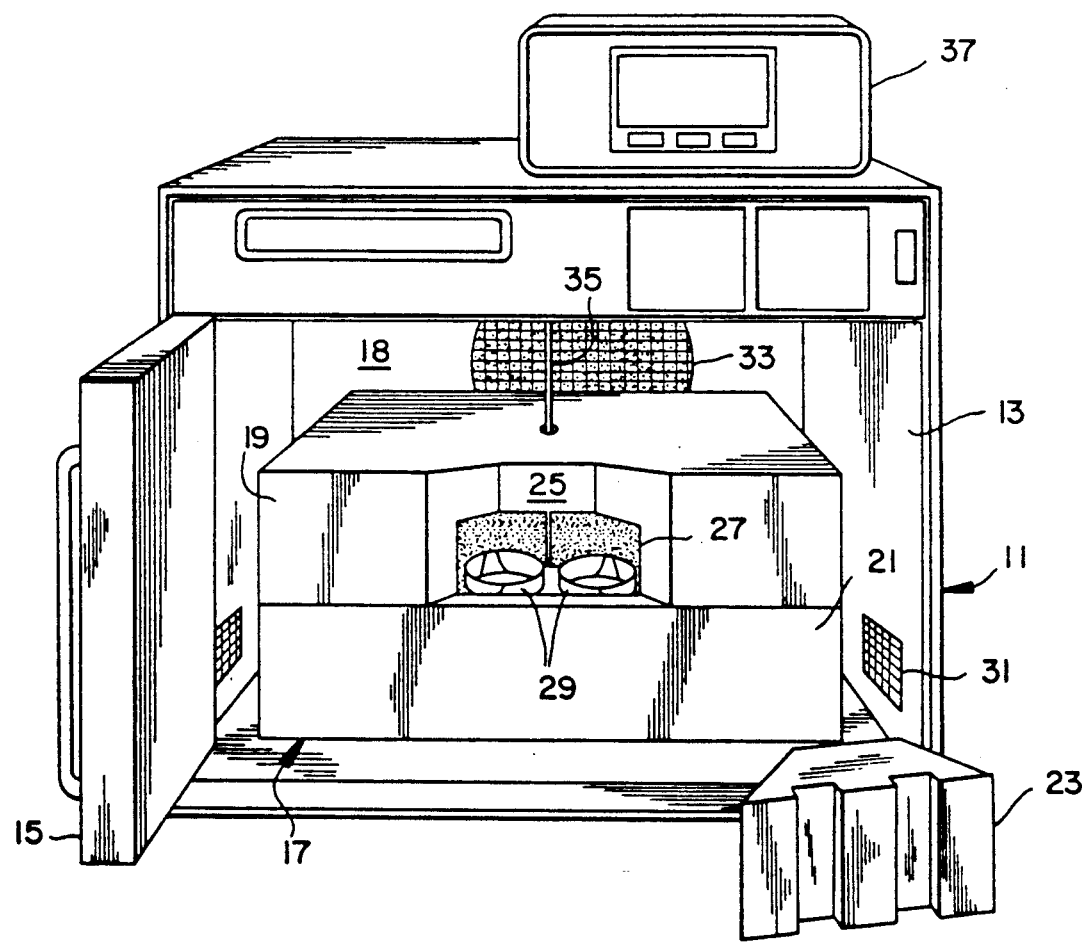
FIG. 1 is a front perspective view of a microwave ashing apparatus, with chamber door open and with furnace door removed to illustrate two of the invented containers in the furnace.

In FIG. 1 a microwave ashing apparatus 11 comprises top, bottom, side and rear walls, all designated by numeral 13, applied to a side wall, and door 15, which define a microwave retaining chamber 18. Inside the chamber is a furnace 17, which includes top and bottom portions 19 and 21, and a furnace door, 23. Such furnace parts are made of microwave transmissive open celled quartz, which is of low thermal conductivity and is heat resistant, capable of being employed at very high temperatures without deterioration. Such a type material is ECCOFOAM® Q, preferably ECCOFOAM Q-G, which is described in a bulletin entitled ECCOFOAM Plastic and Ceramic Foams, of Emerson and Cumming Canton, Massachusetts, dated March, 1980, hereby incorporated herein by reference. Inside the furnace is a furnace cavity 25 and microwave absorptive material 27 is located in grooves or slots (not shown) in the upper and lower portions 19 and 21, with surfaces thereof even with the internal surfaces that define the furnace cavity. In the furnace cavity are illustrated two of the containers of the present invention, which are designated by numeral 29. Also shown in FIG. 1 are inlets 31 for air to enter the chamber, part of which air will pass through the furnace cavity, but most of which passes around the chamber 18 and serves to cool the walls thereof. Such air exits the chamber through outlet 33. A thermocouple 35 is located in the furnace cavity and is communicated by means of a connector (not illustrated) to temperature controller 37. Both the main microwave generating unit of apparatus 11 and temperature controller 37 include controls and visual displays, which are readily apparent and therefore are not specifically numbered.

Figure 2:
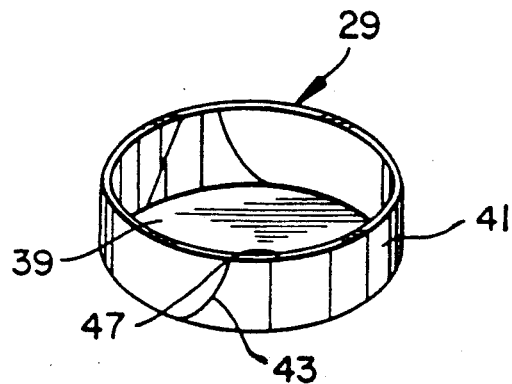
FIG. 2 is a top front perspective view of a walled ashing container of the present invention.

In FIG. 2 there is illustrated one of the containers of the present invention. Such container is of unitary construction, with bottom 39 and side wall 41 being made from the same sheet of porous unwoven quartz microfibers. The container illustrated had been made from a square portion of the fibrous material and includes seam lines like that shown at 43.

Figure 3:
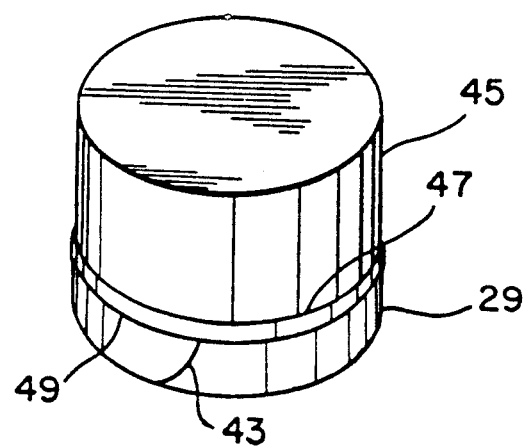
FIG. 3 is a top front perspective view of an ashing container of the present invention having the side wall thereof formed about a mandrel.

In FIG. 3 there is illustrated a step in the manufacture of container 29. As shown, the non-woven microfibrous quartz sheet has been formed about the base of cylindrical mandrel 45 and extra material has been trimmed off along top edge 47. A quartz monofilament 49 or an elastic band or similar restraining means holds the porous microfibrous quartz sheet tightly to the mandrel during the forming operation but is later removed, following normal manufacturing procedure. After shaping of the sheet, it is wetted, formed tightly around the mandrel, trimmed removed from the mandrel and air dried, after which it is heated (fired) to produce the form-retaining container of this invention. While air drying is preferred it may sometimes be omitted Although the invented container is illustrated as a short cylinder, other container shapes may also be produced, utilizing correspondingly shaped mandrels Thus, containers of rectangular or square horizontal cross-sections may be produced. Although various shapes of containers may be made it will be preferred that such containers be relatively flat, usually being of a height/major horizontal dimension ratio less than 1:1 and preferably no more than 1:2. Such ratios, as for height/diameter, may be in the range of 1:10 to 1:2, preferably being in the range of 1:5 to 2:5, elg., about 1:5 or 3:10. While various sizes of containers may be employed, when such containers are flat and cylindrical it will normally be preferred for them to be from 2 to 10 cm. in diameter, preferably 4 to 6 cm., and 0.5 to 4 cm. high, preferably 1 to 2 cm. high.

The unitary container made is heat resistant (high temperature stable), light in weight, microwave transmissive and porous, and is made of quartz microfibers which are held together in walled container form. The quartz microfibers are in thin sheet form, preferably being non-woven, and are heat shaped or fired to form-retaining container shape. The microfibrous quartz sheet will be one of a thickness in the range of 0.2 to 0.7 mm., of such porosity that the pressure drop across it is 1 to 5 mm. of mercury at 5 cm./sec. face velocity of air, resistant to high temperatures, such as up to 500° C., without any adverse effects, retentive of micron size particles, transmissive of microwave radiation, and of a weight in the range of 50 to 200 g./m.². Preferably the material will be of a thickness in the range of 0.3 to 0.6 mm., of such porosity that the pressure drop across it is 2 to 4 mm. of mercury at 5 cm./sec. face velocity of air, resistant, although with some embrittlement, to high temperatures, up to 1,000° C., retentive of over 99% of micron size particles, transparent to microwave radiation, and of a weight in the range of 75 to 125 g./m.². Such a container will normally weigh in the range of 0.2 to 0.6 g., preferably weighing 0.3 to 0.5 g.

A very suitable material of construction for the present containers is that sold by Whatman Laboratory Products, Inc., Clifton, New Jersey, for use as air pollution filters, under the name Whatman ® Ultra-Pure QM-A Quartz Filters, which are described in their publication No. 860-QM-AA (2 pages), which is hereby incorporated herein by reference. According to such publication, the described material is an ultra-pure quartz microfiber filter sheet which contains a small proportion (5%) of conventional borosilicate glass microfibers, which are in the sheet for papermaking purposes. Such publication does not describe or suggest the use of the mentioned material as a container, does not refer to ashing of analytical samples, and does not mention the use of microwave heating for ashing such samples or for ashing other materials. According to the Watman publication the weight of the QM-A quartz filter is 85 g./m.², its thickness is 0.45 mm., it retains 99.999% of 0.6 micron particles at 5 cm./sec. face velocity of air, it is of a dry tensile strength, for a 1.5 cm. wide strip, of 250 to 300 g., and it is capable of withstanding a maximum temperature of 500° C. Also according to such data sheets the material contains 0.2 p.p.m. of cadmium, 1.1 p.p.m. of cobalt, 1.6 p.p.m. of chromium, 3.4 p.p.m. of copper, 23.0 p.p.m. of iron, 0.5 p.p.m. of mangenese, 3.4 p.p.m. of nickel, 2.3 p.p.m. of lead and 18.2 p.p.m. of zinc, which analysis qualifies it as an ultra-pure filter material.

To make the present containers a relatively simple process is employed, in which a non-woven sheet of the described microfibrous quartz is shaped, wetted, formed, trimmed, removed from mandrel, air dried and fired. It the restraint and mandrel material(s) is/are sufficiently heat resistant the firing may be conducted while the sheet material is held in place on the mandrel. Such heating is to a sufficiently high temperature to result in a form-retaining container which temperature will normally be at least 400° C. but is preferably in the range of 500 to 1,200° C. Heating time at the desired "curing" temperature will normally be in the range of 1 to 20 minutes, with ranges of 1 to 15 minutes and 5 to 12 minutes being preferred and more preferred. For example, a 10 minute heating period at about 800–900° C. is often employed. It has been theorized that during the curing operation the borosilicate glass component of the microporous quartz filter material is removed leaving a formed container of quartz fibers which are still porous and which are even more heat resistant than the starting material. However, applicant is not bound by such theory.

The described heating or firing of the container may be effected in various heating means, including ovens and muffle furnaces, but preferably is conducted in a microwave ashing furnace of the type in which the container is primarily intended to be employed. Preferably the heating will be to a temperature at least as high as that to which the container will be subjected during ashing operations, but lower temperatures can also suffice. Moistening of the sheet material may be effected before shaping, as well as after and such moistening may be by spraying, roll application or immersion. It will usually be preferable to limit the amount of moisture on the microporous quartz material being shaped to that amount which is effective to facilitate its shaping to desired container form, which amount will usually be that which is sufficient to wet all such material. Drying before firing may be conducted on or off the mandrel, and may be by hot air, radiant heating or other means, in addition to ambient air drying.

When a mandrel or other form for the microporous sheet is not used during firing to form retaining configuration, as when a flaring dish shape is desired, the sheet may be formed to such a shape and during heating the outer edges thereof may be unsupported or may be supported, as by the upper walls of a larger cylinder. Various types of forms may be employed, including sleeves between which the desired container walls are held during heating, but for the manufacture of the preferred relatively short cylindrical containers a corresponding cylindrical mandrel, like that illustrated in FIG. 3, will preferably be utilized. Such mandrel may be of any suitable material, including various glasses, plastics, metals and alloys, such as copper, brass, steel and stainless steel, but if the mandrel is to be in place during firing it should also be heat resistant. If the heating of the shaped sheet on the form is to be carried out in a microwave ashing apparatus, in which the presence of metals will often be avoided, the form is desirably of a microwave transparent material, such as quartz, although various ceramics and glasses may also be employed under proper circumstances. Whichever firing procedure is followed, it will be satisfactory, providing that the container wall does not collapse or distort objectionably.

The heating or firing is preferably undertaken in a microwave ashing apparatus like that described in the previously mentioned co-pending patent application of Collins and Hargett, which operation is convenient and puts the containers made to a test which almost duplicates actual use conditions. Heating in such apparatus will normally be to the range of about 800° to 1,000° C., e.g., 850° or 950° C., but may be in the previously mentioned range of 500° to 1,200° C. and can even be as low as 400° C. or as high as 1,600° C. under some circumstances.

It will be noted that in the foregoing recitation of firing temperatures many are in excess of the maximum temperature listed by the manufacturer of the quartz filters, which is 500° C. Surprisingly, applicant has found that his containers can be made to be shape-retentive by heating to temperatures close to or in excess of the temperature given by the manufacturer as the maximum temperature to which the filters should be raised. During such heating operation the formerly flat sheet of filter material is converted to a form-retaining container, useful to hold ashable samples for microwave ashing operations. Such permanent shaping of the sheet material takes place at temperatures below the melting point of quartz and the porous sheet does not lose its porosity due to fusion. It appears that the presence of the small proportion of borosilicate glass microfibers in the quartz sheet is helpful in manufacturing the present containers but such is not considered to be essential for obtaining the desired result. It is considered that other glasses may be substituted for the borosilicate glass or that such glasses may be omitted, and still, useful form-retaining containers for microwave ash analyses may be made, but it is preferred to utilize the present starting material, containing a small proportion, usually 1 to 10%, of borosilicate glass microfibers.

After heating is completed the container will be removed from the source of heat and will be allowed to cool in air to room temperature. Slow cooling is favored to relieve strains and to avoid excessive embrittlement. Cooling times (to room temperature) from 30 seconds to ten minutes are considered to be useful to produce satisfactory microwave ashing containers.

In use, a container of the present invention, singly or with other such containers, and sometimes with an insert of similar material, is weighed, has ashable sample added to it, after which it is again weighed, has solution of dispersing agent, such as ethanol solution of magnesium acetate, applied to the ashable specimen, while in the container, and then the sample is ashed in a microwave ashing apparatus, such as that illustrated in FIG. 1, which apparatus is described in more detail in the previously referred to co-pending Collins and Hargett patent application. After completion of ashing the container of ash, with the ash on magnesium oxide [the "ash" from the magnesium acetate), is weighed and the amount of ash and the percentage thereof in the original analytical sample are calculated.

Although the ashing temperature in the microwave ashing apparatus may be in excess of the 500° C. maximum temperature specified by the filter manufacturer, it has been found that the invented container can be satisfactorily employed in high temperature ashing without deterioration sufficient to adversely affect the accuracy of the ash content determination. In fact, the same container can be used for a plurality of microwave ashing analyses, often more than 5 and up to 50, e.g., 10. With continued use the container may become more brittle but if handled carefully it will be employable in the numbers of analyses mentioned without losing desired porosity for such ashing, without breaking and without leaking sample or ash.

In addition to the unexpected advantage of high temperature utility the containers of the present invention possess several other unexpected advantages and characteristics that make them ideal for microwave ashing and microwave ashing analyses. The microfibrous quartz material employed is porous, and allows air to pass through it without resulting in loss of sample or ash. This is important because it promotes ignition and oxidation of the sample (most of the ash being in the form of oxides). When a dispersing agent, such as magnesium acetate in ethanol, is employed to treat the ashable sample before ashing, the porosity of the container material (which is maintained despite the high temperature heating thereof in the forming operation), is believed to contribute to smooth flaming of the solvent, rather than what resembles an explosive combustion of the solvent, which could carry away some of the sample. Such smooth flaming is believed to occur because the ethanol of the magnesium acetate solution spreads over the container due to the container's absorptive properties. The smooth flaming or combustion may also be partially attributable to the relatively low height of the container wall, which facilitates access of air to the sample and to the ethanol present. With the present containers such flaming can be effected in the furnace of the microwave apparatus during the automated ashing operations whereas when ordinary non-porous crucibles of quartz, porcelain or platinum are employed in muffle furnaces or in microwave ashing furnaces, when suitable, it is usually desirable to remove the alcohol from the sample by flaming it externally of the furnace before beginning the ashing operation.

In addition to being porous, the present containers are light in weight and are of low thermal conductivity. Because they are light in weight their weights are often significantly less than the sample weights and may even be less than the ash weights, in some instances, which leads to more accurate weighings of the sample and ash. Furthermore, despite low thermal conductivity the lighweight and porous container cools faster when removed from the ashing furnace, so time is saved in cooling the container and ash before weighing, compared to when an ordinary crucible is employed. The invented containers, being thinner than ordinary crucibles and other containers, more readily transfer heat to ashable samples from external heat sources, such as microwave absorptive heating elements and refractory muffle furnace walls.

Because the invented containers have side walls, they are superior to the flat sheet of support pads described in U.S. Pat. No. 4,565,669, and do not require cover pads to prevent loss of feathery ash into the exit air passing through the furnace and retaining chamber of the microwave ashing apparatus. The wall has the desired effect of allowing access of oxidizing air to the sample while at the same time diminishing its velocity, so as to prevent any loss of ash from the container. However, as a safety measure, if it should be desired, a cover can be employed on the present containers, which may be made of the same material, shaped to suit, or may be of a more open porous material or screening, preferably of quartz filament or fibers.

The following examples illustrate but do not limit the present invention. Unless otherwise indicated, all parts are by weight and all temperatures are in ° C.

EXAMPLE 1

A 9 cm.×9 cm. square of Watman Ultra-Pure QM-A quartz filter, which is a non-woven sheet of quartz microfibers, is shaped about a glass substantially cylindrical form to a flat cylinder with a base about 6 cm. in diameter, and then the cylinder is wetted with about 3.0 g. of water which is applied by spraying it substantially evenly over the surfaces of the filter material. An elastic band is then applied to the cylinder wall, as illustrated in FIG. 3, to hold such wall in position. The application of water to the filter helps it to retain the cylindrical shape. Subsequently, the filter is trimmed and the elastic band is removed. Then the cylinder is removed, and is air dried and then is heated (or fired) in a muffle furnace for about ten minutes at about 870° C. to cure it, after which it is removed from the muffle furnace and allowed to cool in room temperature air. The result is a form-retaining, heat shaped, short cylindrical container, useful for microwave ashing of ashable materials, such as analytical specimens. The container looks like that of FIG. 2 and those of FIG. 1. Although the container is form-retaining, even during use at elevated temperatures as a container for ashable material during microwave ashing thereof, it retains its desirable porosity.

Alternatively, the container may be fired in a microwave ashing furnace like that illustrated in FIG. 1, at a higher temperature, 950° C., and the result is the same.

EXAMPLE 2

An ashing container in flat cylindrical form, essentially the same as that of Example 1 and FIG. 2, is made by wetting a 9 cm.×9 cm. square of the same QM-A filter material with the same amount of water, forming it by means of a quartz mandrel, as shown in FIG. 3, into a flat cylinder, trimming such cylinder to desired 1.5 cm. height, and holding a side wall thereof to the mandrel by means of a quartz thread, also as illustrated in FIG. 3. The shaped cylinder, on the quartz mandrel, is then subjected to a curing heating to a temperature of 950° C. for ten minutes in a microwave furnace, like that of FIG. 1, after which the heating is discontinued and the mandrel and flat cylindrical container are removed from the microwave furnace and allowed to cool in room temperature air. After cooling, the container is removed from the mandrel and is ready for use with the thread in place or after removal thereof.

EXAMPLE 3

(Use of Invented Container in Microwave Ashing Apparatus)

The container described in Example 1, which weighs 0.50 g., has added to it 2.01 g. of a check sample of wheat flour (from the American Association of Cereal Chemists) and to the sample in the container there is applied approximately 3 ml. of a 15 g./l. ethanol (95%) solution of magnesium acetate, in such manner as to wet all the sample (and also to wet part of the container). The container of test sample, wetted with the magnesium acetate solution, is placed in the microwave ashing furnace of FIG. 1 (described in more detail in the co-pending Collins-Hargett patent application, previously mentioned herein) after such apparatus furnace is brought to a temperature of 935° C. and heating at such temperature is continued for ten minutes. Such heating is then halted and the container of ash is removed. The weight of flour ash and magnesium oxide is 0.02 g. and the weight of magnesium oxide (previously obtained experimentally for the volume of solution added) is 0.01 g. Thus, the cereal ash weighed 0.01 g., which corresponds to 0.05% of ash, which checks (to that degree of accuracy) with results obtained by standard muffle furnace ashing (over a 90 minute period) and analysis of the same sample.

In variations of this experiment containers produced by the procedure described in Example 1 as alternative, and by the procedure illustrated in Example 2 are substituted and the results are the same. Furthermore, when a plurality of samples is ashed at the same time, in a plurality of such containers in a microwave ashing apparatus, such as illustrated in FIG. 1, accurate results for each are also obtainable.

EXAMPLE 4

Containers within the invention that are made from a microfibrous filter paper that does not contain borosilicate glass (which is present in the QM-A filter material) can also be made by the processes described, with suitable heating temperatures being employed in the range of 500 to 1,000° C., such as 950° C., and will be satisfactory, even when only half the water is applied and when no water is applied beforehand (other suitable liquids, such as ethanol, may be substituted). Such containers are employable in microwave ashing apparatuses like those illustrated in FIG. 1 and in the co-pending Collins-Hargett application, and accurate analytical results are obtainable, as is verifiable by comparison with standard muffle furnace analyses of the same test samples.

In addition, ash analyses of other materials, including other grain flours, synthetic organic polymeric plastics, such as polyethylene and polypropylene, stream sediments, waste water sludges, coal, milk powder and many other ashable materials, are successfully performable using the described procedures and apparatuses. In such ashings the ashing temperature is varied within a 500 to 1,000° C. range and the ashing times are also varied, usually from 8 to 20 minutes, which will depend on the type of material being ashed and its ashing temperature. In all such instances satisfactory ashings and analyses are the results, which correspond with determinations made following standard muffle furnace procedures applied to the same test specimens Such good results are also obtained when the cylinder is covered by a flat cylindrical cover of the QM-A filter material, but use of such cover is not necessary (although it may be considered to be a safety measure, to make sure that no ash is lost in the exhaust air).

The invention has been described with respect to illustrations, working embodiments and descriptions thereof but is not to be limited to these because it is evident that one of skill in the art, with the present specification before him, would be able to utilize substitutes and equivalents without departing from the invention.

What is claimed is:

1. A container for an ashable material which is to be ashed by heat in an ashing furnace, which container is heat resistant during ashing operations in which it is heated to a temperature up to 500° C., light in weight, porous and includes integral bottom and side wall portions made of quartz microfibers which are held together in walled and bottomed container form.

2. A container according to claim 1 wherein the material of construction thereof is a non-woven thin sheet of quartz microfibers, which sheet has been heat cured or sintered to walled and bottomed container form.

3. A container for an ashable material to be ashed by heating in an ashing furnace, which container is suitable for use in an ashing furnace that is heated by microwave radiation of microwave absorptive elements thereof, which is heat resistant, walled, light in weight, microwave transmissive and porous and is made of a material of construction which is a non-woven thin sheet of quartz microfibers, which are held in walled container form, which sheet is of a thickness in the range of 0.2 to 0.7 mm., of such porosity that the pressure drop across it is 1 to 5 mm. of mercury at 5 cm./sec. face velocity of air, resistant to high temperatures, up to 500° C., retentive of micron size particles, transmissive of microwave radiation and of a weight in the range of 50 to 200 g./m.², which thin sheet of quartz microfibers has been heat cured to walled container form.

4. A container according to claim 3 wherein the material of construction is of a thickness in the range of 0.3 to 0.6 mm., of such porosity that the pressure drop across it is 2 to 4 mm. of mercury at 5 cm./sec. face velocity of air, resistant, with some embrittlement, to high temperatures, up to 1,000° C., retentive of over 99% of micron size particles, transparent to microwave radiation, and of a weight in the range of 75 to 125 g./m.².

5. A container according to claim 4 which is of substantially flat cylindrical form, with the height/diameter ratio thereof being in the range of 1:5 to 2:5 and with the weight of the container being in the range of 0.2 to 0.6 g.

6. A container according to claim 5, which is especially suitable for microwave ashing of samples for ash analyses of materials, in which the cylinder measures 4 to 6 cm. in diameter and 1 to 2 cm. high and weighs 0.3 to 0.5 g.

7. A process for manufacturing a container that is suitable for use as a container for ashable material to be ashed by heat in a furnace in analytical operations, which container is heat resistant during such ashing operations in which it is heated to a temperature up to 500° C., light in weight, porous and includes integral bottom and side wall portions made of quartz microfibers which are held together in walled and bottomed container form, which comprises shaping quartz microfibers to bottomed and side walled container form while such fibers are wet with water, heating such quartz fibers to an elevated temperature to drive off the water and cure or sinter the fibers together, and cooling the container to room temperature, to form the form retaining, light weight, side walled and bottomed, heat resistant container.

8. A process according to claim 7 wherein the heating is for 1 to 20 minutes and after completion of heating the container is cooled to room temperature in room temperature air.

9. A process according to claim 7 wherein the quartz fibers are in the form of a sheet before shaping to container form, such sheet is wet with water before heating and heating is to a temperature in the range of 500 to 1,200° c.

10. A process according to claim 9 wherein the porous sheet of quartz microfibers contains 2 to 10% of borosilicate glass microfibers.

11. A process according to claim 7 wherein the container is resistant to elevated temperatures, up to 1,000° C., porous enough to allow gas flow through the walls thereof during ashing operations, and thin walled enough so as to cool quickly after ashing operations, and during the process for manufacturing heating is to a temperature in the range of 500 to 1,200° C. for 1 to 20 minutes and cooling is to room temperature in room temperature air.

12. A process for manufacturing a container that is suitable for use as a container for ashable material to be ashed by heat from microwave radiation of microwave absorptive elements in an ashing furnace, which comprises shaping a light weight, microwave transmissive and porous sheet of quartz microfibers, which contains 2 to 10% of borosilicate glass microfibers and is of a thickness in the range of 0.2 to 0.7 mm., of such porosity that the pressure drop across it is 1 to 5 mm. of mercury at 5 cm./sec. face velocity of air, resistant to high temperature, up to 500° C., retentive of micron size particles, transmissive of microwave radiation and of a weight in the range of 50 to 200 g./m.², to container form, wetting such sheet with water before heating the sheet in container form, heating the formed container to a temperature in the range of 500° to 1,200° C. for 1 to 20 minutes, and cooling the container to room temperature in room temperature air, whereby a form retaining ashing container results.

13. A process according to claim 12 wherein the porous sheet is of a thickness in the range of 0.3 to 0.6 mm., of such porosity that the pressure drop across it is in the range of 2 to 4 mm. of mercury at 5 cm./sec. face velocity of air, resistant, with embrittlement, to high temperatures, up to 1,000° C., retentive of over 99% of micron sized particles, transparent to microwave radiation, and of a weight in the range of 75 to 125 g./m.².

14. A process according to claim 13 wherein the container resulting is of substantially flat cylindrical form, with the height/diameter ratio thereof being in the range of 1:5 to 2:5 and with the weight of the container being in the range of 0.2 to 0.6 g.

15. A process according to claim 14 wherein the container resulting is especially suitable for microwave ashing of samples for ash analyses of materials, and in which the container resulting is a cylinder measuring 4 to 6 cm. in diameter and 1 to 2 cm. high, and weighs 0.3 to 0.5 g.

* * * * *